United States Patent [19]

Timothy

[11] Patent Number: 4,909,797
[45] Date of Patent: Mar. 20, 1990

[54] ENTERAL DELIVERY SET WITH SHADED DRIP CHAMBER

[75] Inventor: Earle J. Timothy, Clinton, Conn.

[73] Assignee: Sherwood Medical Company, St. Louis, Mo.

[21] Appl. No.: 3,955

[22] Filed: Jan. 16, 1987

[51] Int. Cl.⁴ ............................................. A61M 5/16
[52] U.S. Cl. ............................ 604/253; 128/DIG. 13; 73/861.41
[58] Field of Search .................. 604/65, 67, 245, 251, 604/253–255, 122, 246, 252, 403, 405, 407; 128/DIG. 12, DIG. 13; 73/861.41

[56] References Cited

U.S. PATENT DOCUMENTS

| | | | |
|---|---|---|---|
| 3,252,623 | 5/1966 | Corbin et al. | 604/65 |
| 4,018,362 | 4/1977 | Uband | 604/65 |
| 4,038,981 | 8/1977 | LeFevre et al. | 604/253 |
| 4,105,028 | 8/1978 | Sadlier et al. | 73/861.41 |
| 4,343,305 | 8/1982 | Bron | 604/251 |
| 4,673,397 | 6/1987 | Lynn et al. | 604/251 |
| 4,680,977 | 7/1987 | Conero et al. | 604/253 |
| 4,718,896 | 1/1988 | Arndt et al. | 604/253 |

FOREIGN PATENT DOCUMENTS

| | | | |
|---|---|---|---|
| 940790 | 1/1974 | Canada | 604/65 |
| 199919 | 11/1986 | European Pat. Off. | 604/251 |
| 1228983 | 9/1960 | France | 604/251 |

Primary Examiner—Stephen C. Pellegrino
Assistant Examiner—Ralph Lewis
Attorney, Agent, or Firm—Andrew J. Beck; Montgomery W. Smith; Charles Smith

[57] ABSTRACT

A drip chamber for an enteral nutrition system having an optical drip detector is provided with an opaque upper portion to reduce the amount of ambient light entering the optical sensor for the drip detector.

3 Claims, 1 Drawing Sheet

"PRIOR ART"

ENTERAL DELIVERY SET WITH SHADED DRIP CHAMBER

The present invention relates to delivery sets for enteral feeding systems, and more particularly to sets for use with enteral feeding pumps in which means are provided for monitoring the flow of the formula being fed as it passes through a drip chamber.

BACKGROUND OF THE INVENTION

Enteral feeding systems are known in which the operating condition of the system is monitored by sensing the flow of the feed formula as it passes through a drip chamber. In one system, this is accomplished by directing radiant energy from a source through the drip chamber of the delivery set to a sensor. The enteral fluid drops diffract the radiant energy so that the sensor detects a decrease in signal level with each drop. When no drops occur for a period of time, an alarm may be activated to alert nursing personnel that the system needs attention. It has been observed that strong artificial light or direct sunlight entering the radiant energy sensor may cause interference with the drop detecting arrangement and cause a false alarm.

It is an object of the invention, accordingly, to provide a new and improved enteral delivery set which is free from the above-noted deficiencies of the prior art.

Another object of the invention is to provide a new and improved enteral pump delivery set of the above character which incorporates condition-monitoring means that is not adversely affected by the presence of ambient light from an artificial source or from the sun.

SUMMARY OF THE INVENTION

These and other objects of the invention are attained by providing an enteral delivery set having a drip chamber with means for shading the sensor in the pump from extraneous radiant energy, such as light from a nearby lamp or sunlight, while providing free access for radiant energy from the monitoring source. In one embodiment, the drip chamber is tapered downwardly to a tubular outlet and its upper end is closed by a disk-like plug having a tubular inlet for connection to a source of feed formula. The plug has a skirt which extends downwardly inside and near the side wall of the container. The plug and inside skirt are all resistant to the transmission of radiant energy therethrough, particularly radiant energy to which the sensor is intended to respond, and the length of the inside skirt is preferably selected so that when the drip chamber is installed in its correct position in the pump, th bottom edge of the skirt is just above the upper limit of the radiant energy path from the source to the sensor.

In another form of the invention, the length of the inside skirt in the drip chamber is preferably selected so that it extends at least to the lower limit of the radiant energy path from the source to the sensor and it is formed with opposed windows appropriately sized and shaped to permit the radiant energy from the source to pass to the sensor when the windows are aligned with the radiant energy path. Desirably, cooperating key and keyway means may be formed on the drip chamber and the pump to insure assembly of the two with the windows in proper registry with the source and sensor.

The invention may be better understood from the following detailed description of a representative embodiment, taken in conjunction with the accompanying drawings, in which.

DESCRIPTION OF PREFERRED EMBODIMENTS

Figure 1A:
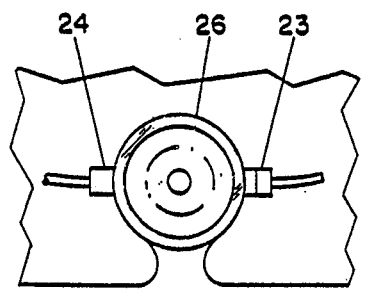
FIG. 1A is a partial view in section taken along the line 1A—13 1A looking in the direction of the arrows.
Figure 1:
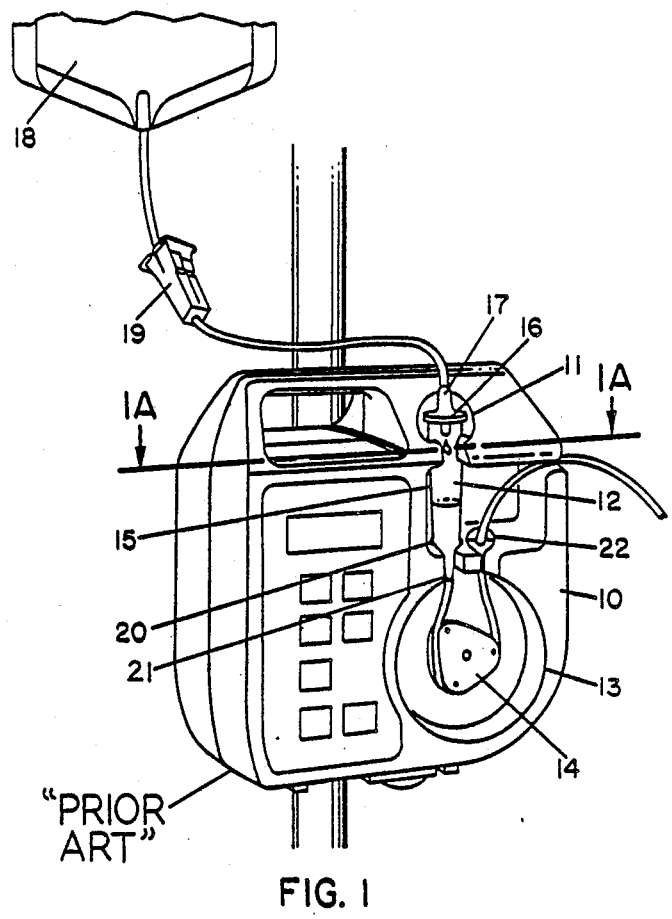
FIG. 1 is a front elevational view of a typical enteral feeding pump in which the enteral delivery set of the invention may be used.

Referring first to FIG. 1, a typical enteral feeding pump comprises a case 10 having a recess 11 formed therein to receive a drip chamber 12 and a shallow recess 13 in which is disposed a roller pump element 14 adapted to be driven by motor means (not shown).

The drip chamber 12 comprises a downwardly tapered body 15 having a top closure 16 provided with an input connector 17 connectable to a source 18 of formula to be fed to a patient, a clamp 19 being provided to control the supply of the formula to the drip chamber 12. The lower end of the drip chamber 12 is seated in a recess 20 formed in the case 10 and it has an outlet connector 21 connected to tubing which is adapted to be stretched around the rollers of the pump 14 and retained in a recess 22 from which it passes to the patient.

The performance of the pump is adapted to be monitored by sensing means including a radiant energy source 23 (FIG. 3) which directs radiant energy through the body of the drip chamber 12 to a sensor 24. The radiant energy source 23 may be of a type LD 273 infrared emitter, and the sensor 24 may be a phototransistor, for example. In the event the tubing becomes occluded or the source 18 becomes depleted so that flow through the drip chamber 12 stops, the output signal from the sensor 24 will no longer have interruptions which can be caused to operate an alarm or to take other corrective action in the known manner.

Figure 2:
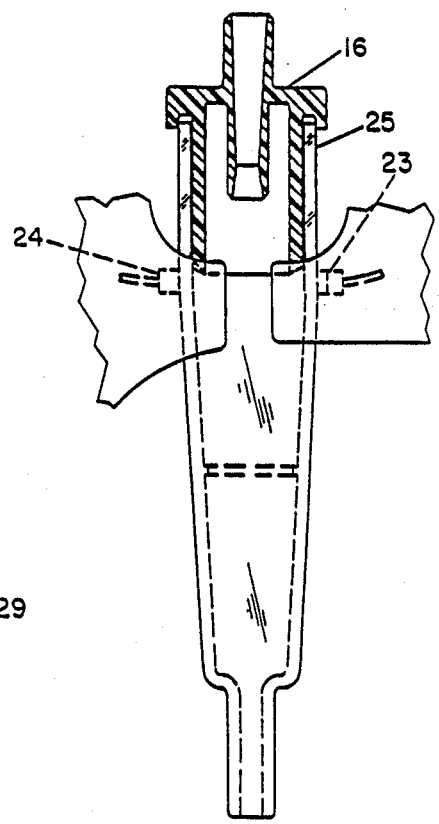
FIG. 2 is a view partially in section of a drip chamber of an enteral delivery set according to the invention for use in a pump of the kind shown in FIG. 1.

When a pump of the kind shown in FIG. 1 is required to be used in the vicinity of close light or sunlight from above, the sensor 24 can be adversely affected so that the signals from emitter 23 can no longer be detected in the presence of bright ambient light. This difficulty has been effectively overcome in accordance with the applicant's invention by providing a drip chamber 12 which is constructed so as to shield the sensor 24 from ambient radiant energy. To this end, the disk-like closure 16 for the drip chamber 12 is provided with a downwardly extending skirt 25 (FIG. 2) of such length that it terminates just above the radiant energy transmission path between the source 23 and the sensor 24 when the drip chamber 12 is seated in the operating position in the recess 11 in the case 10, and both the skirt and the disk-like closure are made of material that is either opaque or at least does not substantially transmit incandescent light or sunlight. Immediately below the lower end of the skirt 25, the sensor 24 is shielded by the adjacent wall 26 of the pump body against which the drip chamber is snugly fitted.

Figure 3:
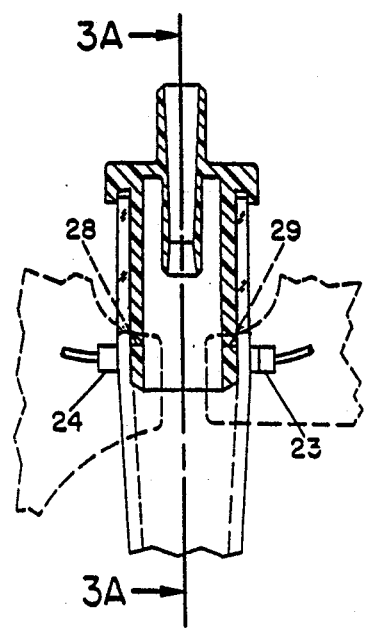
FIG. 3 is a view partially in section of another form of drip chamber according to the invention.
Figure 3A:
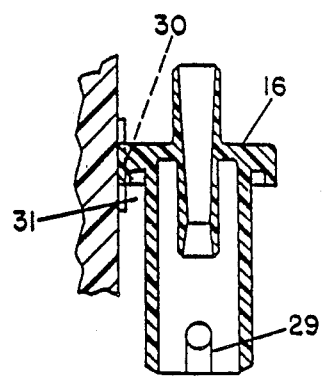
FIG. 3A is a partial view in section taken along the line 3A—3A of FIG. 3 looking in the direction of the arrows.

In the form of the invention shown in FIG. 3, the skirt 27 on the closure 16 extends below the transmission path for radiant energy passing between the source 23 and the sensor 24, registering slots 28 and 29 being provided in the skirt 27 to permit the radiant energy to pass. As best shown in FIG. 3A, the slots 28 and 29 should be of a width just sufficient to pass the radiant energy beam, and they may be arcuate at the top to conform to the shape of the latter. In this form of the invention, it is, of course, necessary that the drip chamber be properly oriented in the recess 11 in the case 10, and to this end the closure 16 may be provided with a notch 30 which is adapted to receive a ridge 31 formed in the rear wall of the recess 11 when the drip chamber 12 is properly positioned so that radiant energy can pass freely from the source 23 to the sensor 24.

The invention thus provides an effective disposable enteral delivery set for an enteral pump that is not susceptible to malfunction when the device is used in the vicinity of bright incandescent light or sunlight. Shading of the sensor from extraneous radiant energy might also be accomplished by making the upper wall of the drip chamber out of material opaque to ambient radiant energy or by coating the surface of the wall with a material either opaque or having low transparency to ambient. Other modifications in form and detail are possible within the scope of the following claims.

I claim:

1. An enteral delivery set for use with an enteral feeding pump having a recess to receive the drip chamber of an enteral feeding set, and radiant energy responsive means disposed at a predetermined level in said pump recess for sensing an operating condition in said drip chamber, comprising an elongated, downwardly tapering drip chamber having a closure at its upper end provided with an inlet connectable to a source of feed and having an outlet at its lower end, at least part of said drip chamber lying above said sensing means when the drip chamber is disposed in the pump recess being resistant to the transmission of radiant energy; said closure for the drip chamber comprises a disk-like cap having a skirt extending into the upper end of the drip chamber at least to the level of said sensing means when the drip chamber is received in said pump recess, said cap and said skirt being resistant to the transmission of radiant energy therethrough; said skirt extends below the level of said sensing means when the drip chamber is received in said pump recess and windows are formed on opposite sides of said skirt in the vicinity of the level of said sensing means, said windows defining a radiant energy transmission path across said drip chamber.

2. An enteral delivery set as in claim 1 in which said windows are shaped as slots extending upwardly from the bottom of said skirt to accommodate said sensing means, said slots being in registering relation so as to define a radiant energy transmission path across said drip chamber.

3. An enteral delivery set as in claim 2, with means in said drip chamber to facilitate assembly of said drip chamber in said pump recess, with said windows and said sensing means in accurate alignment.

* * * * *